United States Patent [19]
Bergman et al.

[11] Patent Number: 5,624,427
[45] Date of Patent: Apr. 29, 1997

[54] FEMALE COMPONENT FOR REFASTENABLE FASTENING DEVICE

[75] Inventors: Carl L. Bergman, Loveland; Kimberly A. Dreier; Miguel A. Robles, both of Cincinnati; Donald C. Roe, West Chester; Mark J. Kline; Margaret H. Hasse, both of Cincinnati, all of Ohio

[73] Assignee: The Procter & Gamble Company, Cincinnati, Ohio

[21] Appl. No.: 374,269

[22] Filed: Jan. 18, 1995

[51] Int. Cl.$^6$ .................................. A61F 13/15; A61F 13/20
[52] U.S. Cl. ...................... 604/391; 604/385.2; 428/105; 428/107; 428/109; 428/182; 24/442
[58] Field of Search .................. 24/442, 443, 449–452; 428/99, 105, 107, 109, 137, 166, 167, 182, 100; 604/373, 385.2, 386, 391, 392, 358, 385.1

[56] References Cited

U.S. PATENT DOCUMENTS

| | | |
|---|---|---|
| 3,255,749 | 6/1966 | Smithers . |
| 3,277,547 | 10/1966 | Billarant . |
| 3,319,307 | 5/1967 | Marforio . |
| 3,665,922 | 5/1972 | Skora . |
| 3,694,867 | 10/1972 | Stumpf . |
| 3,708,833 | 1/1973 | Ribich et al. . |
| 3,863,304 | 2/1975 | Brumlik . |
| 3,895,797 | 7/1975 | Moore . |
| 4,596,568 | 6/1986 | Flug . |
| 4,600,618 | 7/1986 | Raychok, Jr. et al. . |
| 4,654,246 | 3/1987 | Provost et al. . |
| 4,707,893 | 11/1987 | Hashizume et al. . |
| 4,725,473 | 2/1988 | Van Gompel et al. . |
| 4,739,635 | 4/1988 | Conley et al. . |
| 4,761,322 | 8/1988 | Raley . |
| 4,846,815 | 7/1989 | Scripps . |
| 4,963,140 | 10/1990 | Robertson et al. . |
| 5,032,122 | 7/1991 | Noel et al. . |
| 5,151,092 | 9/1992 | Buell et al. . |
| 5,242,436 | 9/1993 | Weil et al. . |
| 5,326,612 | 7/1994 | Goulait . |
| 5,330,458 | 7/1994 | Buell et al. . |
| 5,380,313 | 1/1995 | Goulait et al. . |
| 5,518,801 | 5/1996 | Chappell et al. .......................... 428/167 |

FOREIGN PATENT DOCUMENTS

| | | |
|---|---|---|
| 0233364 | 8/1987 | European Pat. Off. . |
| 0258015 | 3/1988 | European Pat. Off. . |
| 0341993 | 11/1989 | European Pat. Off. . |
| 1140576 | 1/1969 | United Kingdom . |
| 1299897 | 12/1972 | United Kingdom . |
| WO92/20250 | 11/1992 | WIPO . |
| WO95/08311 | 3/1995 | WIPO . |
| WO95/33390 | 12/1995 | WIPO . |

*Primary Examiner*—P. Zuttarelli
*Attorney, Agent, or Firm*—David M. Weirich; Steven W. Miller; Jacobus C. Rasser

[57] ABSTRACT

The present invention provides a refastenable fastening device including female fastening component preferably comprising a base web and an engaging layer. The base web comprises a structural elastic-like film (SELF) web and is joined to the engaging layer which comprises a plurality of filaments or a nonwoven web. The SELF web exhibits an elastic-like behavior in the direction of elongation without the use of added elastic materials. The SELF web includes a strainable network having at least two distinct regions comprised of the same material composition. The first region is oriented substantially parallel to an axis of elongation such that it will undergo a molecular-level deformation in response to an applied axial elongation in a direction substantially parallel to the elongation axis before a substantial portion of the second region undergoes any substantial molecular-level deformation. The second regions initially undergo a substantially geometric deformation in response to an applied elongation in a direction substantially parallel to the axis. The second regions include a plurality of raised rib-like elements which act in conjunction with the filaments or nonwoven web to provide a more effective female component with an increased ability to entangle the hooks of a complementary male component.

13 Claims, 7 Drawing Sheets

FEMALE COMPONENT FOR REFASTENABLE FASTENING DEVICE

FIELD OF THE INVENTION

The present invention relates to hook and loop type fastening devices, and more particularly, to low cost, elastically extensible female fastening components for hook and loop type fastening devices.

BACKGROUND OF THE INVENTION

Refastenable fastening devices of the hook and loop type are currently used widely in a great number of situations. Such refastenable fastening devices have been particularly useful in clothing, disposable absorbent articles, and the like. Such devices are used when it is desirable to create a refastenable bond between two or more articles or between several surfaces of the same article. In certain applications, these refastenable fastening devices have replaced conventional buckles, zippers, buttons, snaps, tie fasteners, and sewing.

A popular type of mechanical fastener currently in wide use which utilizes mechanical entanglement to create a refastenable bond is sold under the trademark "VELCRO". VELCRO fastening devices are described in greater detail in U.S. Pat. Nos. 2,717,437, 3,009,235, 3,266,113, 3,550,837, 4,169,303, and 4,984,339.

VELCRO fasteners utilize two components. A male component and a female component. (The male components are often referred to as the hook or engaging components and the female components are often called loop or landing zone components.) The male component contains a plurality of resilient, upstanding hook shaped elements. The female component generally consists of a fabric containing a plurality of upstanding loops on its surface. When the male component and the loop component are pressed together in a face to face relationship to close the fastening device, the hooks entangle the loops forming a plurality of mechanical bonds between the individual hooks and loops. When these bonds have been created, the components will not generally disengage under normal conditions. This is because it is very difficult to separate the components by attempting to disengage all the hooks at once. However, when a gradual peeling force is applied to the components, disengagement can be easily effected. Under a peeling force, since the hooks are comprised of a resilient material, they will readily open to release the loops.

This type of fastening device has been found especially useful on disposable articles such as disposable garments, disposable diapers, disposable packages, cartons, and the like. Such fastening devices provide a secure closing means, however, the use of existing fastening devices of this type on disposable articles has been limited due to the fact that such fastening devices are relatively costly. A major reason that such fastening devices are costly is that they have high manufacturing costs. These high manufacturing costs are associated with both the hook and loop components of these devices.

Conventional hook and loop components are typically formed by making a fabric with a number of woven loops extending outwardly from a backing. The loops may be provided by weaving a base fabric containing supplementary threads to from the loops, or by knitting the loops into a fabric. The male components of such fastening devices are typically formed by cutting the loops to form hooks. However, these processes generally produce costly hook and loop fastening materials because they are relatively slow. The hook and loop components of such fastening devices are also usually made out of the same relatively expensive material.

Therefore, several attempts have been made to make alternative types of female components for fastening devices. However, such attempts have generally suffered from a number of drawbacks.

U.S. Pat. No. 3,694,867 issued to Stumpf on Oct. 3, 1972, discloses a "separable clasp" having a female component that comprises a "high loft" nonwoven fabric and a backing layer of consolidated flexible adhesive. However, the loop component disclosed in the Stumpf patent is prepared by performing the steps of: (1) activating an open pattern adhesive in which the fibers are imbedded, (2) consolidating the adhesive into a substantially continuous backing layer, and (3) simultaneously looping portions of the fibers such that the fibers form individual loops that extend outwardly from the backing. The female component disclosed in this patent suffers from the drawback that it is made by processes that involves mechanically manipulating fibers in the form of loops. Thus, the female components described therein do not appear to be significantly less expensive to manufacture than conventional loop components.

U.S. Pat. No. 4,761,318 issued to Ott, et al. on Aug. 2, 1988, discloses a loop fastener that can contemporaneously be both formed and also attached to a substrate without the need for any additional steps such as sewing or utilizing pressure sensitive adhesives to affix it to the substrate. However, the Ott loop fastener comprises a fibrous structure having a multiplicity of loops that is adhered to a layer of thermoplastic resin. Thus, the process disclosed in this patent suffers from the drawback that heat must be applied to bond the fibrous structure to the backing.

U.S. Pat. No. 3,708,833 issued to Ribich, et al. on Jan. 9, 1973, discloses a refastenable fastening device having a female component that comprises reticulated urethane foam secured to a backing layer. The female component disclosed in the Ribich, et al. patent suffers from the drawback that foams typically do not have enough openings for the hooks of conventional male components to penetrate. In addition, reticulated foam generally does not have sufficient strength to hold such hooks when forces are applied to the fastening device. Further, manufacturing reticulated foam is a relatively expensive process.

U.S. Pat. No. 5,032,122 issued to Noel, et al. on Jul. 16, 1991, discloses a loop fastening material having a backing of orientable material and a multiplicity of fibrous elements extending from the backing. The fibers are secured to the backing while the backing is in a dimensionally unstable state. The backing is then caused to be transformed to its dimensionally stable state thereby shearing the fibrous elements to form the catching regions of the loop material.

Although the Noel patent discloses an acceptable low cost loop fastening material, the search has continued for more economical loop fastening materials and methods for producing such materials.

Thus, it is an object of the present invention to provide an improved landing zone component for a refastenable hook and loop type fastener.

It is a further object of the present invention to provide a refastenable fastening device having a unique fluted female component.

It is a still further object of the present invention to provide a refastenable fastening device that achieves a strong hold, yet has a female component that is elastically extensible.

It is a further object of the present invention to provide a female component for a hook and loop type fastening device which comprises a structural elastic-like film (SELF) web.

It is yet another object of the present invention to provide a female component for a fastening device that can be used with both commercially available male components having resilient individual hooks, as well as less expensive male components with more brittle hooks than those currently in use.

These and other objects of the present invention will be more readily apparent when considered in reference to the following description and when taken in conjunction with the accompanying drawings.

SUMMARY OF THE INVENTION

The present invention provides a refastenable fastening device including female fastening component preferably comprising a base web and an engaging layer. The base web comprises a structural elastic-like film (SELF) web and is joined to the engaging layer which comprises a plurality of filaments or a nonwoven web. The SELF web exhibits an elastic-like behavior in the direction of elongation without the use of added elastic materials. The SELF web includes a strainable network having at least two distinct regions comprised of the same material composition. The first region is oriented substantially parallel to an axis of elongation such that it will undergo a molecular-level deformation in response to an applied axial elongation in a direction substantially parallel to the elongation axis before a substantial portion of the second region undergoes any substantial molecular-level deformation. The second regions initially undergo a substantially geometric deformation in response to an applied elongation in a direction substantially parallel to the axis. The second regions include a plurality of raised riblike elements which act in conjunction with the filaments or nonwoven web to provide a more effective female component with an increased ability to entangle the hooks of a complementary male component.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Overall Characteristics of the Refastenable Fastening Device

Figure 1:
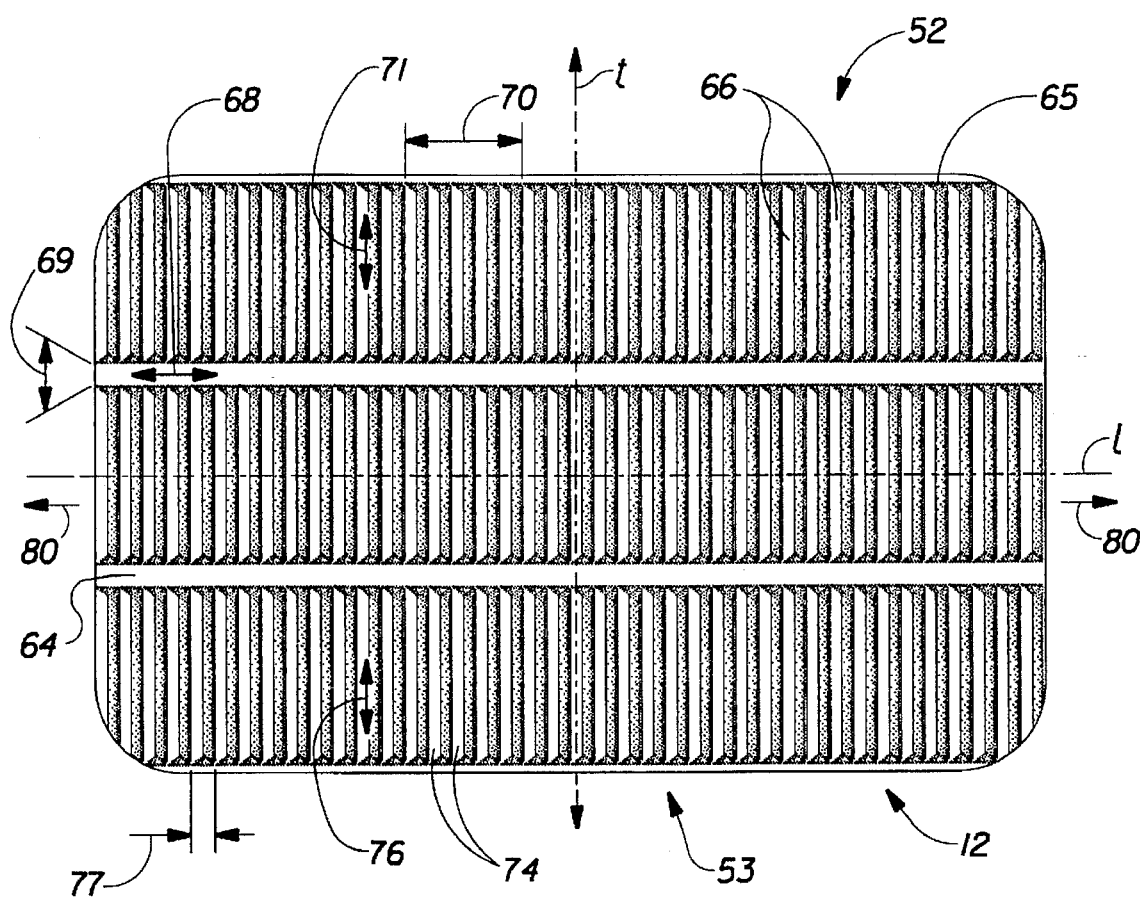
FIG. 1 is a plan view illustration of a preferred embodiment of the base web of the present invention comprising a SELF web with the raised rib-like elements facing toward the viewer.
Figure 1A:
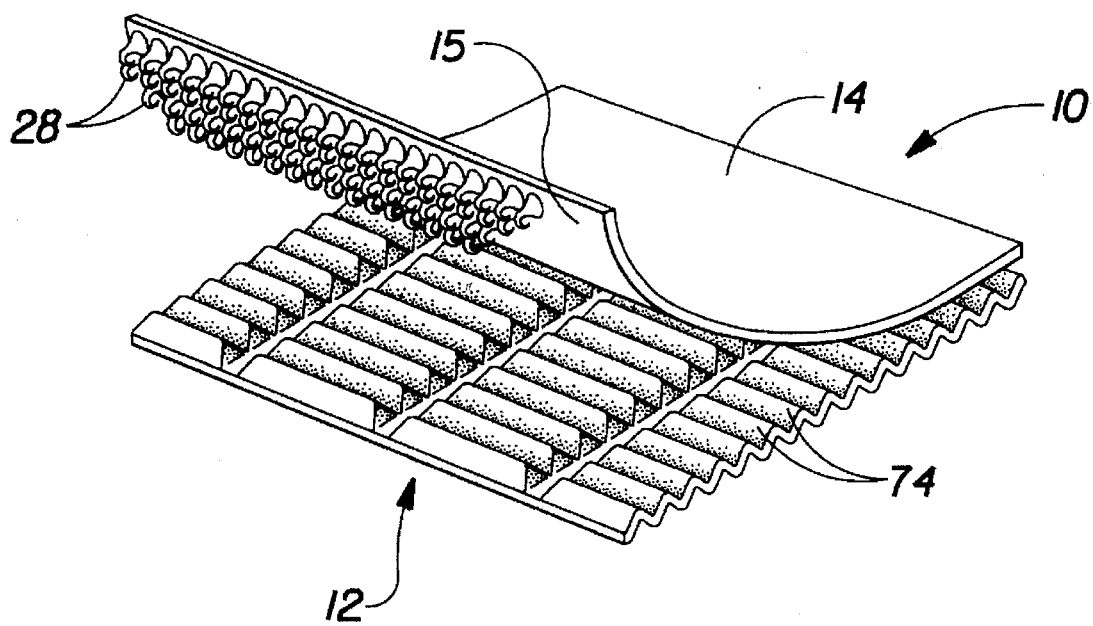
FIG. 1A is perspective illustration of a fastening device embodiment comprising the female component of the present invention.

A preferred embodiment of the refastenable fastening device of the present invention, fastening device 10, is shown in FIG. 1A. The fastening device 10 comprises a female component 12 and a complementary male component 14.

Figure 8:
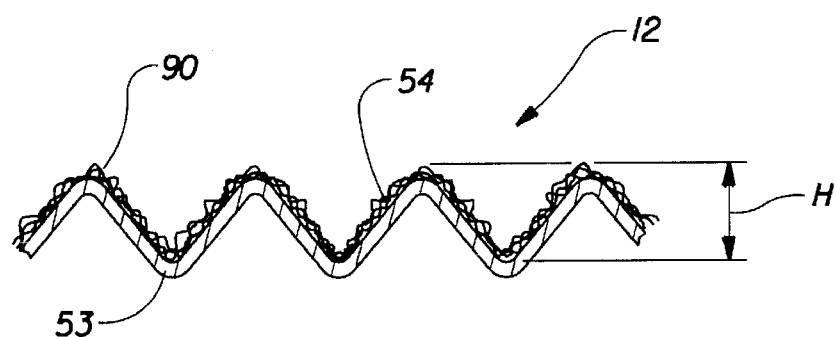
FIG. 8 is a segmented side view of a preferred embodiment of the present invention.

The female component 12 comprises a base web 53 and an engaging layer 54, as shown in FIG. 8. The engaging layer 54 preferably comprises a plurality of filaments 90. As used herein, the term "filament" defines a member having a high ratio of length to diameter or width. Thus, a filament may be a fiber, a thread, a strand, a yarn or any other member or combination of these members, including filaments that are preattached together in nonwoven webs, as are known in the art. Suitable materials for filaments include natural fibers such as cotton or wool; synthetic fibers such as nylon, polyamides, polyesters, polyolefins, polyethylene fibers, polypropylene fibers; spun yarn or any other material or combination of materials known in the art and suitable for use herein. An exemplary nonwoven web is the nonwoven material manufactured by Veratec, Inc., a Division of International Paper Company, of Walpole, Mass. under the designation P-8.

The male component 14, or hook component, comprises a base 15 and a plurality of upstanding engaging elements, or "hooks" 28. The term "hook" is nonlimiting in the sense that the engaging elements may be in any shape known in the art so long as they are adapted to engage the rib-like elements 74 of the female component 12 of the present invention.

The fastening device 10 of the present invention functions in the following manner. The fastening device 10 is closed when the engaging layer 54 of the female component 12 and the hooks 28 of the male component 14 are pressed against each other. The engaging layer 54 of the female component 12 entangles the hooks 28 of the male component 14. (It should be noted embodiments of the female component are contemplated wherein the engaging layer 54 as well as the rib-like elements 74 may entangle the hooks 28.) With the hooks 28 mechanically entangled by the female component 12, the connection between the components resists separating forces that may be exerted on the device 10.

The device 10 is opened by peeling the male component 14 away from the female component 12, or vice versa. If the male component 14 has resilient hooks 28, the peeling action may cause the hooks 28 to be bent such that they disengage from the female component 12. In other cases, the male and female components may be separated by tearing the portion of the female component 12 that is entangling the hooks 28.

In either case, the two components are disengaged and the male component 14 is completely detached from the female component 12. The fastening device 10 is then capable of being refastened in the manner described above.

The Female Component

As stated above, the female component 12 of the present invention comprises an engaging layer 54 including filaments or a nonwoven web and a base web 53. FIG. 1 shows one embodiment of the base web 53 of the female component 12. The base web 53 comprises a structural elastic-like film (SELF) web 52. The SELF web 52 is shown in its untensioned condition. The web has two axes, or centerlines, a longitudinal centerline, l, and a transverse or lateral centerline, t, which is generally perpendicular to the longitudinal centerline.

Figure 2:
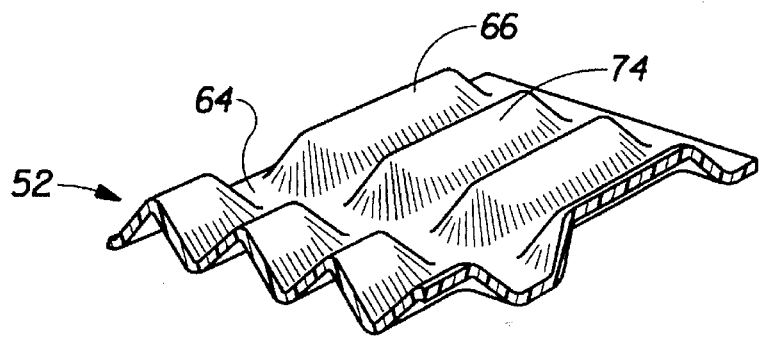
FIG. 2 is a segmented, perspective illustration of the SELF web of FIG. 1 in an untensioned condition.

Referring to FIGS. 1 and 2, the SELF web 52 includes a "strainable network" of distinct regions. As used herein, the term "strainable network" refers to an interconnected and interrelated group of regions which are able to be extended to some useful degree in a predetermined direction providing the SELF web 52 with an elastic-like behavior in response to an applied and subsequently released elongation. Accordingly, the SELF web 52 and thus, the female component are elastically extensible. (As used herein, the term "elastically extensible" refers to the elastic-like behavior that the SELF web 52 exhibits when it is subjected to an applied elongation; it extends in the direction of applied elongation and returns to its substantially untensioned condition once the applied elongation is removed.) Further, the SELF web 52 is able to undergo multiple cycles of applied elongation without losing its ability to substantially recover.)

The strainable network includes at least a first region 64 and a second region 6. The SELF web 52 includes a transitional region 65 which is at the interface between the first region 64 and the second region 66. The transitional region 65 will similarly exhibit complex combinations of behavior of both the first region 64 and the second region 66. It is recognized that the SELF web 52 will have transitional regions, however, the SELF web 52 is largely defined by the behavior of the web material in the distinctive regions (e.g., first region 64 and second region 66). Therefore, the ensuing description of the SELF web 52 will be concerned with the behavior of the web material in the first regions 64 and the second regions 66 only, since it is not significantly dependent upon the complex behavior of the web material in the transitional regions 65.

The SELF web 52 has a first surface and an opposing second surface. In the preferred embodiment shown in FIGS. 1 and 2, the strainable network includes a plurality of first regions 64 and a plurality of second regions 66. The first regions 64 have a first axis 68 and a second axis 69, wherein the first axis 68 is preferably longer than the second axis 69. The first axis 68 of the first region 64 is substantially parallel to the longitudinal axis of the SELF web 52 while the second axis 69 is substantially parallel to the transverse axis of the SELF web 52. Preferably, the second axis of the first region 64, (i.e., the width of the first region 64), is from about 0.01 inches to about 0.5 inches, and more preferably from about 0.03 inches to about 0.25 inches. The second regions 66 have a first axis 70 and a second axis 71. The first axis 70 is substantially parallel to the longitudinal axis of the SELF web 52, while the second axis 71 is substantially parallel to the transverse axis of the SELF web 52. Preferably, the second axis of the second region 66, (i.e., the width of the second region 66), is from about 0.01 inches to about 2.0 inches, and more preferably, from about 0.125 inches to about 1.0 inches. In the preferred embodiment of FIG. 1, the first regions 64 and the second regions 66 are substantially linear, extending continuously in a direction substantially parallel to the longitudinal axis of the SELF web 52. The first region 64 has an elastic modulus E1 and a cross-sectional area A1. The second region 66 has an elastic modulus E2 and a cross-sectional area A2.

As illustrated in FIG. 1, a portion of the SELF web 52 has been "formed" such that the SELF web 52 exhibits a resistive force along an axis, which in the case of the illustrated embodiment is substantially parallel to the longitudinal centerline l of the SELF web 52, when subjected to an applied axial elongation in a direction substantially parallel to the longitudinal centerline l. As used herein, the term "formed" refers to the creation of a desired structure or geometry upon the SELF web 52 that will substantially retain the desired structure or geometry when it is not subjected to any externally applied elongations or forces.

The first region 64 of the SELF web 52 is preferably visually distinct from the second region 66. As used herein, the term "visually distinct" refers to features of the SELF web 52 material which are readily discernible to the normal naked eye when subjected to normal use. Preferably, the first region 64 has a "surface-pathlength" less than that of the second region 66, as measured parallel to a predetermined axis when the material is in an untensioned state. As used herein, the term "surface-pathlength" refers to a measurement along the topographic surface of the region in question in a direction parallel to an axis.

In one preferred embodiment of the SELF web 52 as shown in FIGS. 1 and 2, the first regions 64 are substantially planar. That is, the material within the first region 64 is in substantially the same condition before and after the formation step undergone by the SELF web 52. The second regions 66 include a plurality of raised rib-like elements 74. As used herein, the term "rib-like element" refers to an embossment, debossment or combination thereof which has a major axis and a minor axis. The rib-like elements 74 have a first or major axis 76 which is substantially parallel to the transverse axis of the SELF web 52 and a second or minor axis 77 which is substantially parallel to the longitudinal axis of the SELF web 52. The first axis 76 of the rib-like elements 74 is at least equal to, and preferably longer than the second axis 77. Preferably, the ratio of lengths of the first axis 76 to the second axis 77 is at least about 1:1, or greater, and more preferably at least about 2:1 or greater. The major axes of the rib-like elements 74 are preferably oriented substantially perpendicular to the axis of applied elongation. The major axis and the minor axis of the rib-like elements 74 may each be linear, curvilinear or a combination of linear and curvilinear. As used herein, the term "substantially perpendicular" refers to an orientation between two axes whereby the subtended angle formed by the two axes or an extension of the two axes is greater than 45°. In the case of a curvilinear element it may be more convenient to use a linear axis which represents an average of the curvilinear element.

The rib-like elements 74 allow the second region 66 to undergo a substantially "geometric deformation" which results in significantly less resistive forces to an applied elongation than that exhibited by the "molecular-level deformation" of the first region 64. As used herein, the term "molecular-level deformation" refers to deformation which occurs on a molecular level and is not discernible to the normal naked eye. That is, even though one may be able to discern the effect of a molecular-level deformation, e.g., elongation of the SELF web 52, one is not able to discern the deformation which allows or causes it to happen. This is in contrast to the term "geometric deformation". As used herein, the term "geometric deformation" refers to deformations of the SELF web 52 which are generally discernible to the normal naked eye when the SELF web 52 or articles embodying the SELF web 52 are subjected to an applied elongation. Types of geometric deformation include, but are not limited to bending, unfolding, and rotating.

The rib-like elements 74 in the second region 66 may be separated from one another by unformed areas, essentially unembossed or debossed, or simply formed as spacing areas. Preferably, the rib-like elements 74 are adjacent one another and are separated by an unformed area of less than 0.10 inches as measured perpendicular to the major axis 76 of the rib-like element 74, and more preferably, the rib-like element 74 are contiguous having no unformed areas between them.

The first region 64 and the second region 66 each have a "projected pathlength". As used herein, the term "projected pathlength" refers to length of a shadow of a region that would be thrown by parallel light. The projected pathlength of the first region 64 and the projected pathlength of the second region 66 are equal to one another.

The first region 64 has a surface-pathlength, L1, less than the surface-pathlength, L2, of the second region 66 as measured topographically in a direction parallel to the longitudinal axis of the SELF web 52 while the SELF web 52 is in an untensioned condition. Preferably, the surface-pathlength of the second region 66 is at least about 15% greater than that of the first region 64, more preferably at least about 30% greater than that of the first region 64, and most preferably at least about 70% greater than that of the first region 64.

For the SELF web 52, the direction of applied axial elongation, D, indicated by arrows 80 in FIG. 1, is substantially perpendicular to the first axis 76 of the rib-like elements 74. The rib-like elements 74 are able to unbend or geometrically deform in a direction substantially perpendicular to their first axis 76 to allow extension in the SELF web 52.

Figure 5:
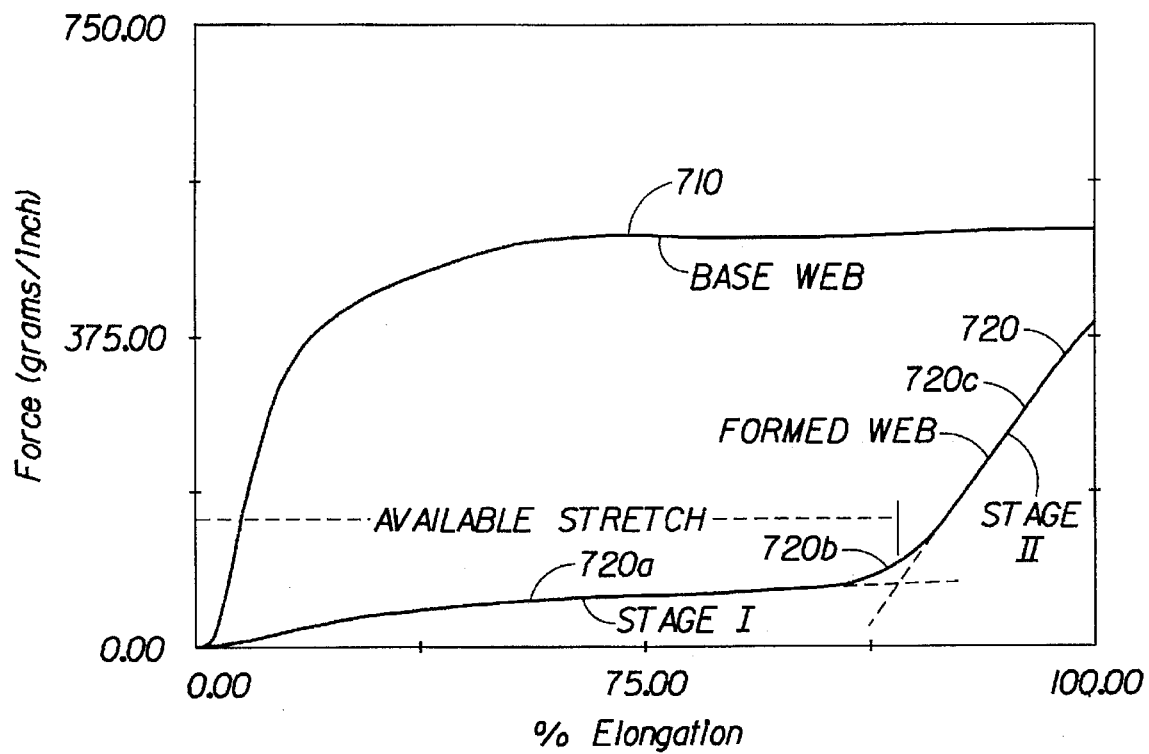
FIG. 5 is a graph of the resistive force versus percent elongation comparing the behavior of the SELF web as shown in FIG. 1, with an otherwise identical, planar, base polymeric web material.

In FIG. 5 there is shown a graph of the resistive force-elongation curve 720 of a formed polymeric SELF web 52 of the present invention along with a curve 710 of a base web material, i.e., not including first and second regions 66, of similar material composition. Specifically, the samples are polymeric web materials comprised substantially of linear low density polyethylene, approximately 0.001 inches thick, marketed under the designation Sample 1401 available from Clopay Corporation of Cincinnati, Ohio.

Referring now to the force-elongation curve 720, there is an initial substantially linear, lower force versus elongation stage I designated 720a, a transition zone designated 720b which indicates the encounter of a force wall, and a substantially linear stage II designated 720c which displays substantially higher force versus elongation behavior.

As seen in FIG. 5, a SELF web 52 having a strainable network exhibits different elongation behavior in the two stages when subjected to an applied elongation in a direction parallel to the longitudinal axis of the SELF web 52. The resistive force exerted by the SELF web 52 to the applied elongation is significantly less in stage I region (720a) versus the stage II region (720c) of curve 720. Further, the resistive force exerted by the SELF web 52 to the applied elongation as depicted in stage I (720a) of curve 720 is significantly less than the resistive force exerted by the base web as depicted in curve 710 within the limits of elongation of stage I. As the SELF web 52 is subjected to further applied elongation and enters stage II (720c) the resistive force exerted by the SELF web 52 increases and approaches the resistive force exerted by the base web. The resistive force to the applied elongation for the stage I region (720a) of the SELF web 52 is provided by the molecular-level deformation of the first region 64 of the SELF web 52 and the geometric deformation of the second region 66 of the SELF web 52. This is in contrast to the resistive force to an applied elongation that is provided by the base web, depicted in curve 710 of FIG. 5, which results from molecular-level deformation of the entire web. SELF web materials can be designed to yield virtually any resistive force in stage I which is less than that of the base web material by adjusting the percentage of the web surface which is comprised of the first and second regions 66, respectively. The force-elongation behavior of stage I can be controlled by adjusting the width, cross-sectional area, and the spacing of the first region 64 and the composition of the base web.

Figure 3:
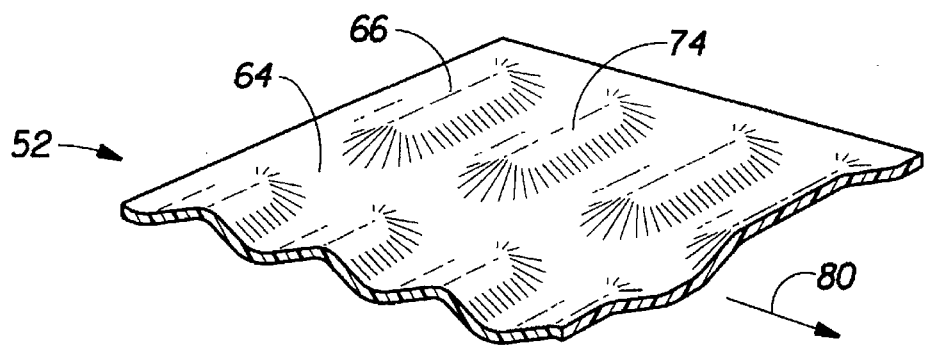
FIG. 3 is a segmented, perspective illustration of the SELF web of FIG. 1 in a tensioned condition corresponding to stage I on the force-elongation curve depicted in FIG. 5.
Figure 4:
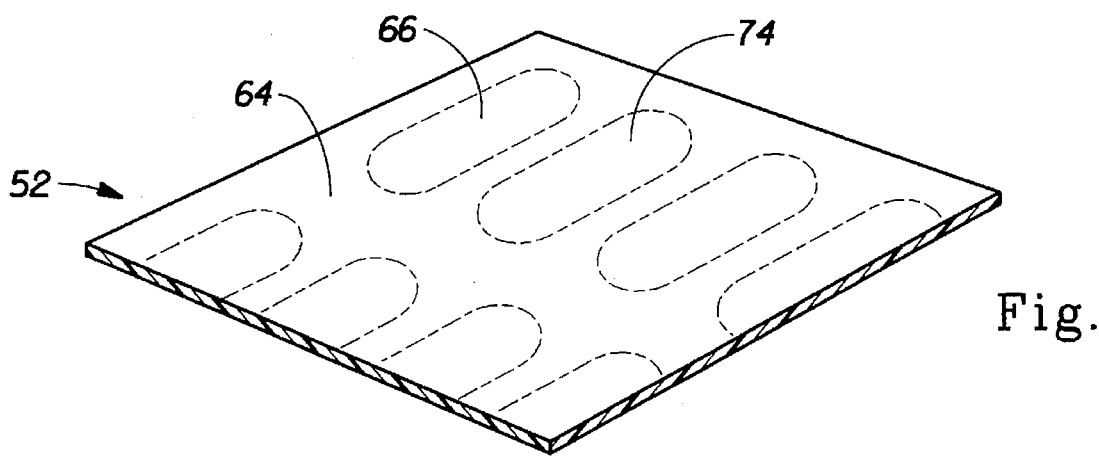
FIG. 4 is a segmented perspective illustration of the SELF web of FIG. 1 in a tensioned condition corresponding to stage II on the force-elongation curve depicted in FIG. 5.

As shown in FIG. 3, as the SELF web 52 is subjected to an applied axial elongation, D, indicated by arrows 80 in FIG. 1, the first region 64 having the shorter surface-pathlength, L1, provides most of the initial resistive force, P1, as a result of molecular-level deformation, to the applied elongation which corresponds to stage 1. While in stage I, the rib-like elements 74 in the second region 66 are experiencing geometric deformation, or unbending, and offer minimal resistance to the applied elongation. In the transition zone (720b) between stages I and II, the rib-like elements 74 are becoming aligned with the applied elongation. That is, the second region 66 is exhibiting a change from geometric deformation to molecular-level deformation. In stage II, as seen in FIG. 4, the rib-like elements 74 in the second region 66 have become substantially aligned with the axis of applied elongation (i.e., the second region 66 has reached its limit of geometric deformation) and begin to resist further elongation via molecular-level deformation. The second region 66 now contributes, as a result of molecular-level deformation, a second resistive force, P2, to further applied elongation. The resistive forces to elongation depicted in stage II by both the molecular-level deformation of the first region 64 and the molecular-level deformation of the second region 66 provide a total resistive three, PT, which is greater than the resistive force depicted in stage I which is provided by the molecular-level deformation of the first region 64 and the geometric deformation of the second region 66. Accordingly, the slope of the force-elongation curve in stage II is significantly greater than the slope of the force-elongation curve in stage I.

The resistive force P1 is substantially greater than the resistive force P2 when (L1+D) is less than L2. While (L1+D) is less than L2 the first region 64 provides an initial resistive force, P1, generally satisfying the equation:

$$P1 = \frac{(A1 \times E1 \times D)}{L1}$$

When (L1+D) is greater than L2 the first and second regions 66 provide a combined total resistive force, PT, to the applied elongation D, generally satisfying the equation:

$$PT = \frac{(A1 \times E1 \times D)}{L1} + \frac{(A2 \times E2 \times |L1 + D - L2|)}{L2}$$

The maximum elongation occurring while in stage I is referred to as the "available stretch" of the SELF web 52.

The available stretch corresponds to the distance over which the second region 66 experiences geometric deformation. The available stretch can be effectively determined by inspection of the force-elongation curve 720 as shown in FIG. 5. The approximate point at which there is an inflection in the transition zone between stage I and stage II is the percent elongation point of "available stretch". The range of available stretch can be varied from about 10% to 100% or more, and can be largely controlled by the extent to which surface-pathlength L2 in the second region 66 exceeds surface-pathlength L1 in the first region 64 and the composition of the base film. The term "available stretch" is not intended to imply a limit to the elongation which the SELF web 52 may be subjected to as there are applications where elongation beyond the available stretch is desired.

Figure 6:
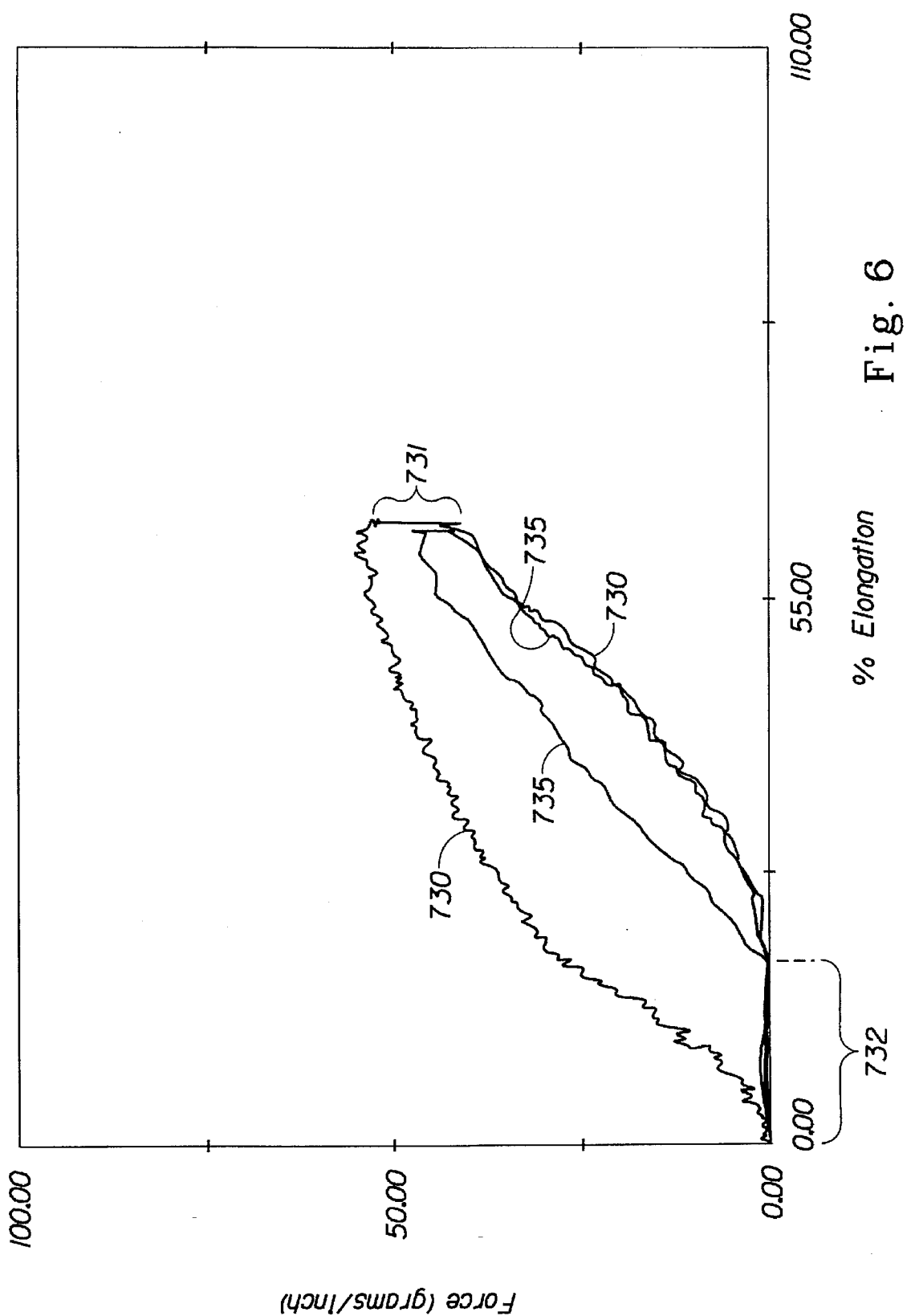
FIG. 6 is a graph of the elastic hysteresis behavior of the SELF web of FIG. 1 when subjected to 60% elongation and examined for hysteresis response.

The curves 730 and 735 in FIG. 6 show the elastic hysteresis behavior exhibited by the SELF web 52 of the present invention which is generally similar to the SELF web 52 used to generate curve 720 in FIG. 5. The SELF web 52 was examined for elastic hysteresis behavior at an elongation of 60%. Curve 730 represents the response to an applied and released elongation during the first cycle and curve 735 represents the response to applied and released elongation during the second cycle. The force relaxation during the first cycle 731 and the percent set or deformation 732 are depicted in FIG. 6. Note that significant recoverable elongation, or useful elasticity, is exhibited at relatively low forces over multiple cycles, i.e., the SELF web 52 can easily expand and contract to a considerable degree.

While the SELF web 52 may be easily and reversibly extended in the direction of applied axial elongation, in a direction substantially perpendicular to the first axis of the rib-like elements 74, the SELF web 52 is not as easily extended in a direction substantially parallel to the first axis of the rib-like elements 74. The formation of the rib-like elements 74 allows the rib-like elements 74 to geometrically deform in a direction substantially perpendicular to the first or major axis of the rib-like elements 74, while requiring substantially molecular-level deformation to extend in a direction substantially parallel to the first axis of the fib-like elements 74.

The amount of applied force required to extend the SELF web 52 is dependent upon the composition and cross-sectional area of the web material forming the SELF web 52 and the width and spacing of the first regions 64, with narrower and more widely spaced first regions 64 requiring lower applied extension forces to achieve the desired elongation. The first axis, (i.e., the length) of the first regions 64 is preferably greater than the second axis, (i.e., the width) of the first region 64 with a preferred length to width ratio of from about 5:1 or greater.

The depth and frequency of rib-like elements 74 can also be varied to control the available stretch of the SELF web 52 and the efficacy of the female component 12 comprising the SELF web 52. The available stretch and the ability of the engaging layer 54 to engage the hooks of a complementary male component 14 are increased if for a given frequency of rib-like elements 74, the height H or degree of deformation imparted on the rib-like elements 74 is increased (the height H is shown in FIG. 8). The same result is achieved if for a given height H or degree of deformation, the frequency of rib-like elements 74 is increased. However, the frequency of the rib-like elements 74 must not be so great that the hooks 28 of the male component are unable to engage the filaments 90 of the female component. In one preferred embodiment of the present invention, the height H of the rib-like elements 74 is between about 0.010 inches and about 0.050 inches (about 0.25 mm and about 1.27 mm), and more preferably between about 0.020 inches and about 0.035 inches (about 0.51 mm and about 0.89 mm).

The SELF web 52 also need not be extensible only in the direction parallel to the lateral centerline of the web. For example, the longitudinal axis and the transverse axis of the SELF web 52 may be disposed at an angle to the longitudinal centerline and lateral centerline of the web. Further, portions of the SELF web 52 may have different angles of extensibility.

The SELF web 52 may be comprised of polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE® available from Dow Chemical Company and EXXACT® available from Exxon and Tredegar CPC2 polyethylene available from Tredegar, Inc.), and breathable polymers. The web materials may also be comprised of a synthetic woven, synthetic knit, nonwoven, apertured film, macroscopically expanded three-dimensional formed film, absorbent or fibrous absorbent material, foam filled composition or laminates and/or combinations thereof. The nonwovens may be made by any of the following methods: spunlace, spunbond, meltblown, carded and/or air-through or calender bonded, or any other methods known in the art.

While the female component may comprise a base web 53 including a SELF web 52 comprising a single layer of substantially planar polymeric film, the present invention may be practiced equally well with SELF webs comprising other materials, laminates of two or more materials or filler materials. (As used herein, the term "filler material" refers to materials that provide the SELF web 52 with bulk or thickness.) Examples of materials from which the SELF web 52 can be made include two-dimensional apertured films and macroscopically expanded, three-dimensional, apertured formed films. Examples of macroscopically expanded, three-dimensional, apertured formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference. Examples of other suitable materials include composite structures or laminates of polymer films, nonwovens, and polymer films and nonwovens. The laminates of polymer films and nonwovens may also comprise absorbent or fibrous absorbent materials, foams, thermally bonded air-laid fibrous structures or other compositions. The addition of layers or filler materials to the SELF web 52 may act to reinforcing the web for strength and recovery benefits as well as help to maintain the rib-like elements 74 in a raised position. This, in turn, helps keep the engaging layer 54 of the female component 12 in a position to better engage the hooks of a complementary male fastening component.

The base web 53 and the engaging layer 54 may be joined to each other or to any other layers or materials by any of a number of bonding methods known to those skilled in the art. Such bonding methods include but are not limited to thermal bonding; adhesive bonding (using any of a number of adhesives including but not limited to spray adhesives, hot melt adhesives, latex based adhesives and the like); sonic bonding; and extrusion laminating whereby a polymeric film is cast directly onto a nonwoven substrate, and while still in a partially molten state, bonds to one side of the nonwoven or where a meltblown nonwoven is directly attached to a polymeric web. Further, the engaging layer may be joined to the base web continuously or intermittently. (As used herein, the term "joined" encompasses configurations whereby an element is directly secured to another element and configurations whereby an element is indirectly secured to another element by affixing an element to intermediate member(s) which are in turn affixed to another element.)

Methods for forming SELF web 52 materials include, but are not limited to, embossing by mating plates or rolls, thermoforming, high pressure hydraulic forming, or casting. Generally, the engaging layer comprising filaments or a nonwoven web is joined to the base web 53 before the SELF web is formed. However, it should be understood that the present invention may be practiced wherein the engaging layer 54 is joined to the base web 53 after the base web 53 has been formed into a SELF web. Further, while the entire portion of the SELF web 52, as shown in FIG. 1 has been subjected to a forming operation, the SELF web 52 may also be subjecting to formation only a portion thereof, e.g., a portion of the landing zone component 12.

Figure 7:
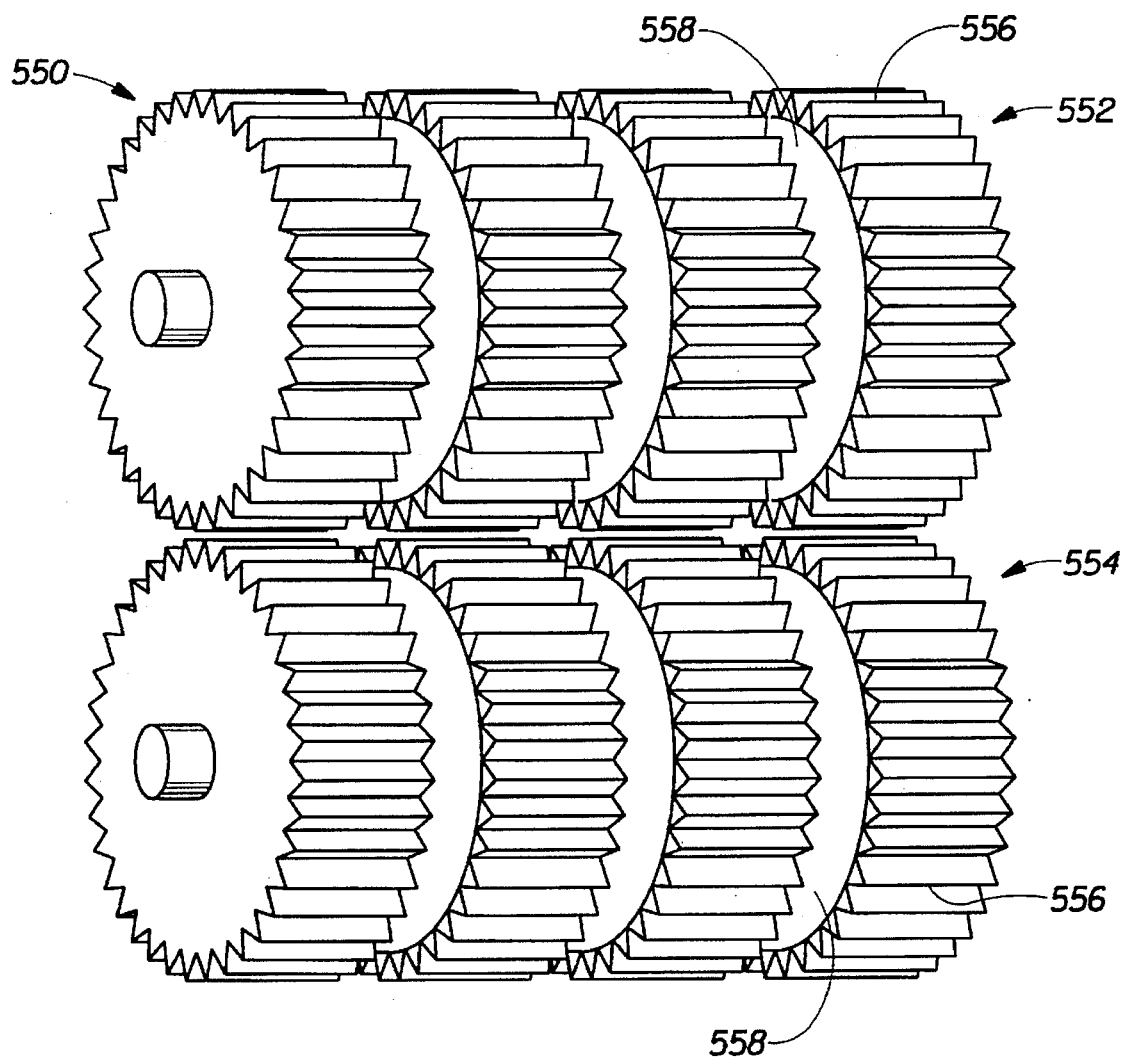
FIG. 7 is a simplified illustration of yet another apparatus used to form at least a portion of a film into a SELF web.

Referring now to FIG. 7, there is shown an apparatus generally indicated as 550 for forming a material into a SELF web 52. Apparatus 550 includes a pair of rolls 552, 554. Rolls 552 and 554 each have a plurality of toothed regions 556 and grooved regions 558 extending about the circumference of rolls 552, 554 respectively. As the material passes between rolls 552 and 554, the grooved regions 558 will leave portions of the material unformed, while the portions of the material passing between toothed regions 556 will be formed producing rib-like elements 74 in second regions 66.

The Complementary Male Component

The term "male component", as used herein, is used to designate the portion of the fastening device 10 having engaging elements, such as hooks 28. The male components 14 used with the nonwoven female component 12 of the present invention can be conventional, commercially available hook materials. The male component 14, however, is not limited to conventional materials with flexible, resilient hooks 28. Suitable male components can have less expensive, relatively inflexible, more brittle hooks. Further, the engaging elements may have any shape known in the art such as hooks, "T's", mushrooms, or any other shape. One suitable male component 24 may comprise a number of shaped engaging elements projecting from a woven backing such as the commercially available material designated "SCOTCHMATE" brand No. FJ3402 available from Minnesota Mining and Manufacturing Company, St. Paul, Minn. A preferred male component is described in U.S. Pat. No. 4,846,815 entitled "Disposable Diaper Having An Improved Fastening Device" which issued to C. L. Scripps on Jul. 11, 1989. Other particularly preferred male components and methods for making the same are the prongs described in U.S. Pat. No. 5,058,247 entitled "Mechanical Fastening Prong" issued to Thomas et al. on Oct. 22, 1991; U.S. Pat. No. 5,116,563 entitled "Process for Producing a Mechanical Fastener" issued to Thomas et al. on May 26, 1992; U.S. Pat. No. 5,180,534 entitled "Process of Manufacturing A Refastenable Mechanical Fastening System", which issued to Thomas, et al. on Jan. 19, 1993; and U.S. Pat. No. 5,230,851 entitled "Process of Manufacturing a Refastenable Fastening System" issued to Thomas on Jul. 27, 1993. Each of these patents are hereby incorporated by reference herein.

The male component 14 may be manufactured from a wide range of materials. Such suitable materials include, but are not limited to, nylon, polyester, polypropylene, or any combination of these or other materials.

Examples of Uses of the Refastenable Fastening Device

The refastenable fastening device 10 of the present invention is especially useful as a fastening device for disposable absorbent articles. The term "disposable absorbent article", as used herein, refers to articles which absorb and contain body exudates. More particularly, the term refers to articles which are placed against or in proximity to the body of the wearer to absorb and contain the various exudates discharged from the body. The term "disposable" means that such articles may be discarded after a single use (i.e., they are generally not intended to be laundered or otherwise be reused). Examples of disposable absorbent articles include diapers, incontinence garments, sanitary napkins, bandages, and the like.

Figures 9, 10:
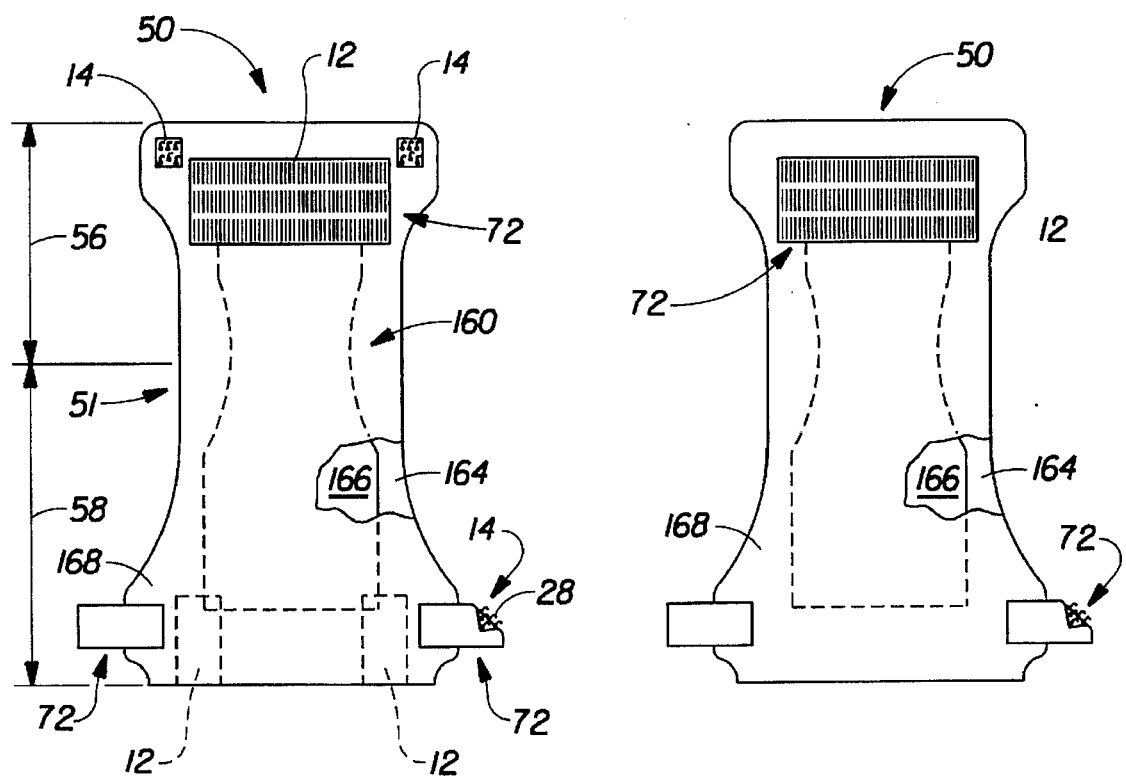
FIG. 9 is a plan view of a disposable absorbent article comprising the female component of the present invention.
FIG. 10 is a plan view of a disposable absorbent article comprising the female component of the present invention.

FIGS. 9 and 10 show an exemplary disposable diaper 50 comprising a fastening system 72 including the female component 12 of the present invention. The diaper 50 preferably comprises a body portion 51 and two waist regions, a first waist region 56, and a second waist region 58. The body portion 51 preferably comprises a a liquid impervious backsheet 168 and a containment assembly 160 preferably including a liquid pervious topsheet 164 and an absorbent core 166.

As shown in FIG. 9, the fastening system 72 of the diaper 50 comprises the female component 12 of the present invention and the male component 14. The positions of the components of the fastening system 72 can vary depending on the desired configuration of the diaper 50. Further, any portion of the backsheet 168 or the entire backsheet 168 may comprise the female component 12 of the present invention providing the diaper 50 with unlimited fastening positions as well as a means for fastening the diaper 50 in a disposal configuration. In other embodiments, the diaper 50 having the backsheet 168 comprising the female component 12 may comprise one or more additional fastening components joined to the backsheet 68. The additional fastening component(s) may comprise the female component 12 of the present invention or any other fastening component(s) as are known in the art including, but not limited to tapes, mechanical fasteners, hook and loop type fasteners, etc.

Several examples of well known diaper configurations to which the present invention can be readily adapted are described in U.S. Pat. Nos. 5,151,092 and 5,221,274 both entitled "Absorbent Article With Dynamic Elastic Waist Feature Having A Predisposed Flexural Hinge", issued to Kenneth B. Buell, et al. on Sep. 29, 1992 and Jun. 22, 1993, respectively; U.S. Pat. No. 3,860,003 issued to Kenneth B. Buell on Jan. 14, 1975; U.S. Pat. No. 5,242,436 issued to Weil et al. on Sep. 7, 1993; and U.S. Pat. No. 5,330,458 issued to Buell et al. on Jul. 19, 1994. Each of these patents is hereby incorporated by reference herein. It should be understood, however, that the fastening device of the present invention is not limited to use with any specific diaper structure or configuration.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A female component of a refastenable fastening device, said female component comprising:

a base web material exhibiting an elastic-like behavior in response to an applied axial elongation along at least one axis thereof, said base web material including a strainable network having first and second regions formed of substantially the same material composition, said first region providing a first, elastic-like resistive force to said applied axial elongation, and said second region providing a second resistive force to further applied axial elongation, said second resistive force being different in magnitude from said first resistive force, thereby providing at least two stages of resistive forces, said second region of said base web having a plurality of raised rib-like elements; and a plurality of filaments joined to said rose web material, whereby said filaments are supported by said rib-like elements such that said filaments are capable of entangling hooks of a complementary male fastening component.

2. The female component of claim 1 wherein said filaments are preattached together in the form of a nonwoven web.

3. The female component of claim 1 wherein said rib-like elements have a height of between 0.010 inches and 0.050 inches.

4. The female component of claim 1 wherein said rib-like elements have a height of between 0.020 inches and 0.035 inches.

5. A disposable absorbent article comprising a topsheet, a backsheet joined with said topsheet, an absorbent core positioned between said topsheet and said backsheet, and a fastening system for fastening said disposable absorbent article about a wearer, wherein said fastening system comprises the female component of claim 1.

6. A disposable absorbent article, comprising: a backsheet and a containment assembly joined with said backsheet, wherein at least a portion of said backsheet comprises the female component of claim 1.

7. The disposable absorbent article of claim 6 wherein said containment assembly comprises a topsheet and an absorbent core.

8. The disposable absorbent article of claim 6 comprising an additional fastening component joined to said backsheet.

9. A refastenable fastening device, comprising:

a) a male component comprising hooks; and b) a female component comprising:

a base web material exhibiting an elastic-like behavior in response to an applied axial elongation along at least one axis thereof, said base web material including a strainable network having first and second regions formed of substantially the same material composition, said first region providing a first, elastic-like resistive force to said applied axial elongation, and said second region providing a second distinctive resistive force to further applied axial elongation, said second resistive force being different in magnitude from said first resistive force, thereby providing at least two stages of resistive forces; said second region of said base web having a plurality of raised rib-like elements; and a plurality of filaments joined to said base web material, whereby said filaments are supported by said rib-like elements such that said filaments are capable of entangling hooks of said male component.

10. The refastenable fastening device of claim 9 wherein said filaments are preattached together in the form of a nonwoven web.

11. The refastenable fastening device of claim 9 wherein said rib-like elements have a height of between 0.010 inches and 0.050 inches.

12. The refastenable fastening device of claim 9 wherein said rib-like elements have a height of between 0.020 inches and 0.035 inches.

13. A disposable absorbent article comprising a topsheet, a backsheet joined with said topsheet, an absorbent core positioned between said topsheet and said backsheet, and a fastening system for fastening said disposable absorbent article about a wearer, wherein said fastening system comprises the refastenable fastening device of claim 9.

* * * * *

UNITED STATES PATENT AND TRADEMARK OFFICE
CERTIFICATE OF CORRECTION

PATENT NO. : 5,624,427  
DATED : April 29, 1997  
INVENTOR(S) : Carl L. Bergman et al.

Page 1 of 1

It is certified that error appears in the above-identified patent and that said Letters Patent is hereby corrected as shown below:

Column 1,  
Line 63, "from" should read -- form --.

Column 5,  
Line 35, "6" should read -- 66 --

Colum 13,  
Line 20, "rose" should read -- base --.

Signed and Sealed this

Twenty-fifth Day of December, 2001

Attest:

JAMES E. ROGAN  
Attesting Officer     Director of the United States Patent and Trademark Office